United States Patent
Rauscher et al.

(10) Patent No.: US 7,058,157 B2
(45) Date of Patent: Jun. 6, 2006

(54) METHOD FOR PRODUCING IMAGES WITH THE AID OF A SPIRAL COMPUTED TOMOGRAPHY UNIT, AND A SPIRAL COMPUTED TOMOGRAPHY UNIT

(75) Inventors: Annabella Rauscher, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 25 days.

(21) Appl. No.: 10/834,271

(22) Filed: Apr. 29, 2004

(65) Prior Publication Data
US 2004/0218711 A1    Nov. 4, 2004

(30) Foreign Application Priority Data
Apr. 29, 2003    (DE)    ................ 103 19 324

(51) Int. Cl.
*A61B 6/00*    (2006.01)
(52) U.S. Cl. ........................ 378/15; 378/901
(58) Field of Classification Search ................ 378/15, 378/19, 901
See application file for complete search history.

(56) References Cited

U.S. PATENT DOCUMENTS

| | | | |
|---|---|---|---|
| 5,377,250 A * | 12/1994 | Hu | .............................. 378/15 |
| 5,684,855 A | 11/1997 | Aradate et al. | ................. 378/4 |
| 5,796,803 A | 8/1998 | Flohr et al. | .................... 378/15 |
| 5,802,134 A | 9/1998 | Larson et al. | .................... 378/4 |
| 6,359,956 B1 * | 3/2002 | Hsieh et al. | ................... 378/15 |
| 6,385,278 B1 * | 5/2002 | Hsieh | ............................. 378/8 |
| 6,563,909 B1 | 5/2003 | Schmitz | ..................... 378/156 |
| 6,647,095 B1 * | 11/2003 | Hsieh | .......................... 378/159 |
| 6,658,081 B1 | 12/2003 | Bruder et al. | ................. 378/15 |
| 2003/0133533 A1 | 7/2003 | Bruder et al. | ................... 378/4 |

FOREIGN PATENT DOCUMENTS

| | | |
|---|---|---|
| DE | 197 11 963 A1 | 11/1997 |
| DE | 199 62 281 A1 | 6/2001 |
| DE | 101 27 269 A1 | 1/2003 |

OTHER PUBLICATIONS

Stierstorfer et al.—"Segmented Multiple Plane Reconstruction: A Novel Approximate Reconstruction Scheme for Multi-Slice Spiral CT" —Institute of Physics Publishing—Phys. Med. Biol. 47 (2002) pp. 2571-2581.*

* cited by examiner

Primary Examiner—David V. Bruce
Assistant Examiner—Jurie Yun
(74) Attorney, Agent, or Firm—Harness, Dickey & Pierce

(57) ABSTRACT

A weighted method is for producing images with the aid of a spiral computed tomography unit. Further, in a CT unit, the detector and beam are tuned to one another in such a way that a drop in dose rate occurs at the edges within the detector. The form of the weighting function corresponds at least approximately to the dose rate characteristic and/or to the characteristic of the signal quality of the detector.

20 Claims, 4 Drawing Sheets

METHOD FOR PRODUCING IMAGES WITH THE AID OF A SPIRAL COMPUTED TOMOGRAPHY UNIT, AND A SPIRAL COMPUTED TOMOGRAPHY UNIT

The present application hereby claims priority under 35 U.S.C. §119 on German patent application number DE 103 19 324.3 filed Apr. 29, 2003, the entire contents of which are hereby incorporated herein by reference.

FIELD OF THE INVENTION

The invention generally relates to a method for producing images with the aid of a spiral computed tomography unit. Preferably, the method includes at least the following method steps:

in order to scan an object to be examined, preferably a patient, with the aid of at least one conical beam emanating from a focus, and with the aid of at least one planar detector, preferably of multirow design with a width B orientated in the z-direction, for the purpose of detecting the at least one beam the at least one focus is moved around the object to be examined on a spiral focal track, the at least one detector supplying output data that correspond to the detected radiation, sectional and/or volume images of the scanned object to be examined are reconstructed from the, if appropriate pretreated, output data, at least one spatial weighting of the data used for the calculation being undertaken for the purpose of reconstruction.

BACKGROUND OF THE INVENTION

Methods for producing images with the aid of spiral CT units are generally known and are described, for, example, in the relevant chapters of the publications "Computertomographie" ["Computed tomography"], Willi A. Kalender, ISBN 3-89578-082-0 and "Bildgebende Systeme für die medizinische Diagnostik" ["Imaging Systems for Medical Diagnostics"], Heinz Morneburg (Editors), ISBN 89578-002-2, the entire content of the disclosure of which is incorporated herein by reference.

A fundamental distinction is made between so-called 2D and 3D reconstruction methods in the case of the known image producing methods. With reference to the 2D reconstruction method, reference is made by way of example to U.S. Pat. No. 5,802,134 and with reference to the 3D reconstruction method reference is made by way of example to the patent application DE 102 48 770.7, which is not a prior publication, the entire contents each of which being incorporated herein by reference. In the case of both methods, it is known to use spatial weighting functions to take account of the data redundancies occurring during scanning with large conical angles of the beam cone in order to improve the reconstruction method. Patent application DE 102 44 181.2, the entire contents of which is incorporated herein by reference, which introduces such a weighting function W(z) or W(q), z corresponding to the z-axis and q to the number of rows of the multirow detector, may be mentioned by way of example with reference to such a spatial weighting.

The proposed weighting functions all exhibit basically the same behavior. They all have the value 1 in the middle of the detector, and fall off to 0 toward the edge of the detector— seen in the z-direction in each case—in order to avoid artifacts that are caused by the sharp detector edges.

A disadvantage of these weightings resides in the fact that they lead to a reduction in the dose usage.

SUMMARY OF THE INVENTION

It is therefore an object of an embodiment of the invention to find both a reconstruction method and a spiral CT unit that in each case permit a better dose usage, and/or avoid characteristic formation of artifacts by the detector edge.

An object is achieved by an embodiment of the invention.

When designing current spiral CT systems with planar or multirow detectors, care is taken to obtain a plateau-type dose rate characteristic that is as uniform as possible over the width of the detector. In order to achieve this, it is necessary for the edge region of the radiation cone, in which the finite extent of the focus means that there is no sharp end, but a continuous drop in the dose rate, to be extended beyond the detector surface. The aim is therefore to keep the region of the so-called penumbra of the dose rate profile outside the detector surface.

The inventors have found that, contrary to prior practice, it is advantageous to select the geometrical arrangement between the radiation cone and detector such that the region of the drop in dose rate at the edge of the radiation cone is also detected by the detector. In this penumbra region, the signals determined by the detector exhibit a higher level of noise, and so they have to be weighted downward in order overall to obtain a measured value with minimum noise. However, this weighting corresponds, on the other hand, to the weighting which is undertaken in any case in order to avoid edge artifacts.

Consequently, by simultaneously including a drop in dose rate in the edge region of the detector and weighting the edge region during the reconstruction, it is possible overall to achieve a reduction in the dose administered to the patient in conjunction with an improvement in the image by comparison with unweighted methods. Thus, the previously unnecessarily strong irradiation of the patient in the edge region of the detector is dispensed with by reducing the size of the radiation cone in relation to the detector surface.

Consequently, in one embodiment the inventors propose an improved method for imaging with the aid of a spiral CT which has the following method steps:

in order to scan an object to be examined, preferably a patient, with the aid of at least one conical beam emanating from a focus, and with the aid of at least one planar detector, preferably of multirow design with a width B orientated in the z-direction, for the purpose of detecting the at least one beam the at least one focus is moved around the object to be examined on a spiral focal track, the at least one detector supplying output data that correspond to the detected radiation, sectional and/or volume images of the scanned object to be examined are reconstructed from the, if appropriate pretreated, output data, at least one spatial weighting of the data used for the calculation being undertaken for the purpose of reconstruction, the detector and beam being tuned to one another in such a way that a drop in dose rate occurs at the edges within the detector, and the form of the weighting function corresponding at least approximately to the dose rate characteristic and/or to the characteristic of the signal quality of the detector.

The geometrical arrangement between the detector and beam is preferably undertaken such that the drop in dose rate occurs exclusively in the z-direction. Thus the edge regions of the detector are not affected in the longitudinal direction by a change in dose rate.

On the one hand, the desired dose rate characteristic can be achieved on the basis of the finite extent of the focus, that is to say the penumbra produced, or it is additionally possible to make use of an appropriately designed shape filter between the focus and detector by which the drop in dose rate can be varied in a desired way. It is possible thereby, for example, to effect an optimum tuning between the characteristic of the dose rate in the z-direction and the weighting function used.

The dose rate characteristic can be designed in this case in such a way that the dose rate vanishes at the edges. The weighting function can, for example, assume an at least largely trapezoidal characteristic.

As already mentioned, the method according to an embodiment of the invention can be integrated both in 2D reconstruction methods and in 3D reconstruction methods.

However, it is particularly preferred to apply the method according to an embodiment of the invention in conjunction with the SMPR method (SMPR=Segmented Multiple Plane Reconstruction), as is described, for example, in patent application DE 102 44 181.2 or in laid-open application DE 101 27 269 A1, the entire contents of each of which is hereby incorporated herein by reference. The formula $$P_{x,y,z}(\theta) = \frac{1}{H} \sum_k \sum_q W(q) \cdot h(d_{x,y,z}(\theta + k\pi, \tilde{p}, q)) \cdot P(\theta + k\pi, \tilde{p}, q)$$

described in the above-named patent application can be used for back projection in the case of the use of parallel data, it holding true for the sum H of the weights h that $$H = \sum_k \sum_q W(q) \cdot h(d_{x,y,z}(\theta + k\pi, \tilde{p}, q)),$$

and W(q) being the weighting function over the detector rows q that is to be adapted according to the invention to the dose rate characteristic $\dot{D}(q)$ over the detector rows q. $\dot{D}(q)$ is preferably directly proportional to W(q). The meaning of the variables is explained in detail in the said application. The disclosure content of this application is incorporated in full.

In accordance with the basic idea of an embodiment of the invention, the inventors also propose to improve a spiral CT unit for scanning an object to be examined with the aid of a beam emanating from at least one focus, and with the aid of a detector. The detector is preferably of planar design and preferably has a multiplicity of distributed detector elements for detecting the rays of the beam to the effect that the detector and beam are tuned to one another in such a way that a drop in dose rate occurs at the edges within the detector. Finally, a device may be provided for carrying out the method outlined above and its particular embodiments. The devices above can further be functional devices, and/or at least partially implemented by programs or program modules.

BRIEF DESCRIPTION OF THE DRAWINGS

The present invention will become more fully understood from the detailed description of exemplary embodiments given hereinbelow and the accompanying drawing figures, which are given by way of illustration only and thus are not limitative of the present invention.

The following designations are used: 1 gantry; 2 focus; 3 beam diaphragm; 4 beam; 5 detector; 6 data/control line; 7 computer; 8 monitor; 9 keyboard; B width of the detector; L length of the detector; P patient; $P_1$–$P_n$ program module; S spiral track; V feed; W weighting. In detail, the figures include.

DETAILED DESCRIPTION OF THE PREFERRED EMBODIMENTS

Figure 1:
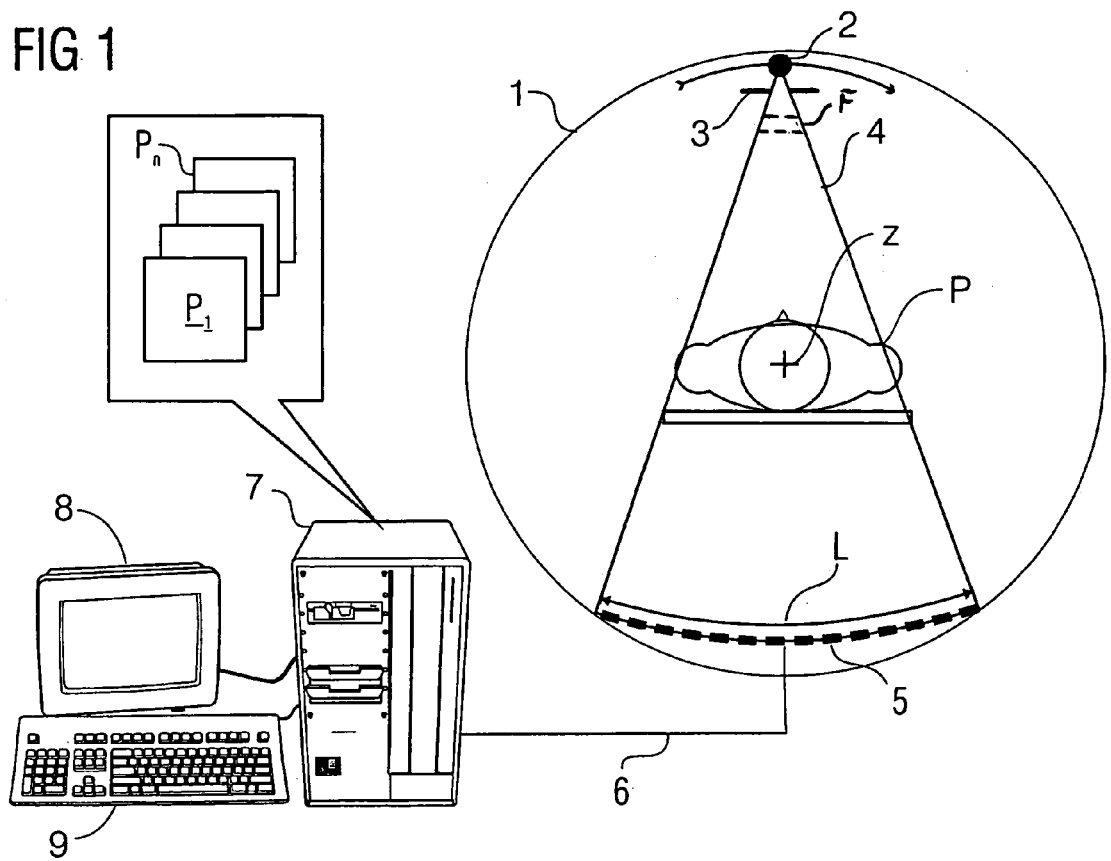
FIG. 1 shows a schematic in the z-direction of a spiral CT unit having several rows of detector elements.
Figure 2:
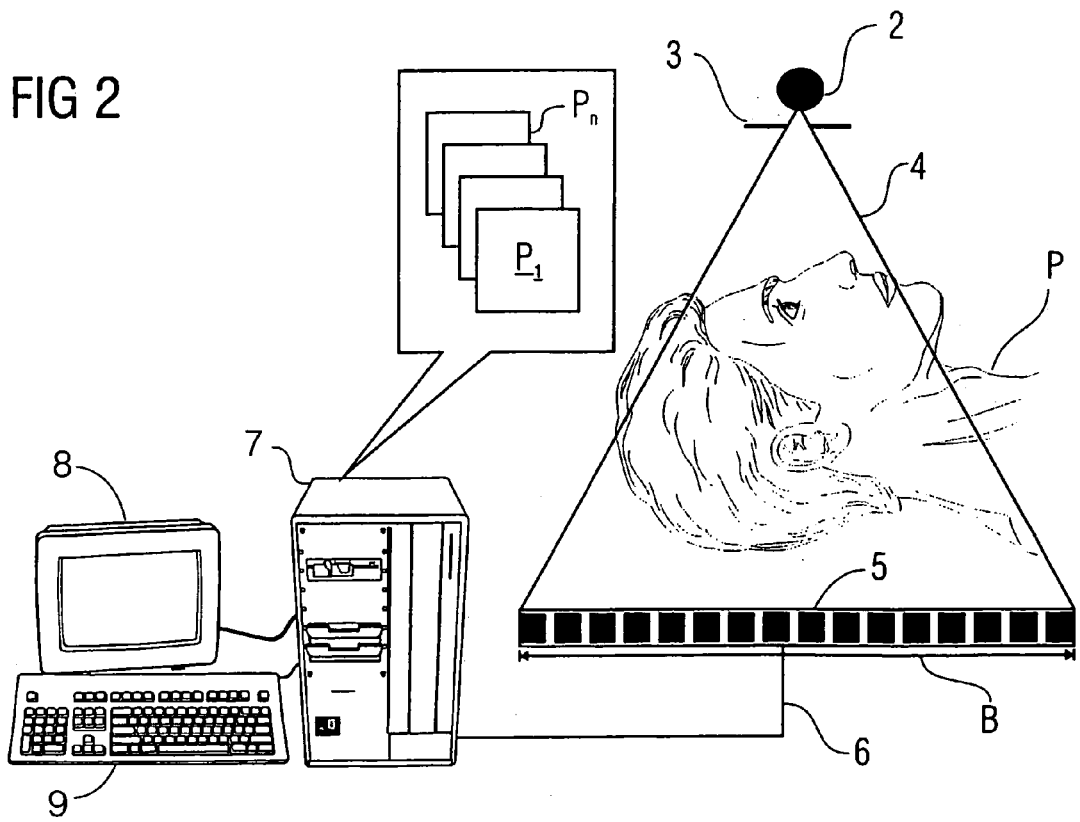
FIG. 2 shows a longitudinal section along the z-axis through the unit in accordance with FIG. 1.

A spiral CT unit suitable for carrying out the method according to an embodiment of the invention and having a multirow detector is illustrated in FIGS. 1 and 2. FIG. 1 shows in a schematic the gantry 1 with a focus 2 and a likewise rotating detector 5 in a section perpendicular to the z-axis, while FIG. 2 shows a longitudinal section in the direction of the z-axis. The gantry 1 has an x-ray source with its schematically illustrated focus 2 and a beam diaphragm 3 near the source and mounted in front of the focus.

Figure 3:
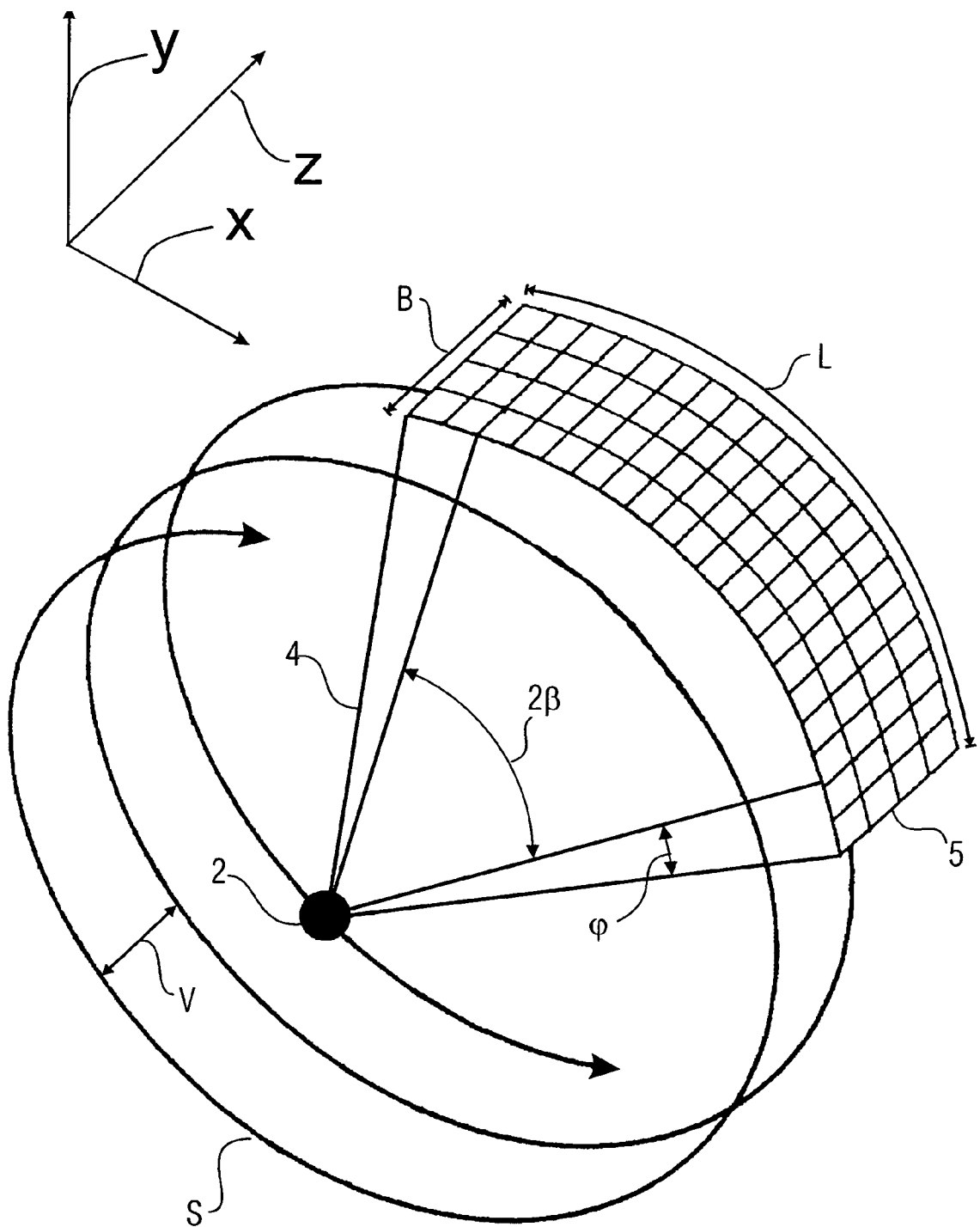
FIG. 3 shows a schematic of the spiral movement of focus and detector.

Starting from the focus 2, a fan shaped beam 4 runs in a fashion delimited by the beam diaphragm 3 to the detector 5 situated opposite, which beam penetrates the patient P lying therebetween. The scanning is performed during the rotation of the focus 2 and detector 5 about the z-axis, the patient P being moved at the same time in the direction of the z-axis. This gives rise in the coordinate system of the patient P to a spiral track S for the focus 2 and detector 5 with a pitch or feed V as illustrated spatially and schematically in FIG. 3. An appropriately designed shape filter F may be located between the focus and detector.

When scanning the patient P, the dose-dependent signals detected by the detector 5 are transmitted to the computer 7 via the data/control line 6. The spatial structure of the scanned region of the patient P is subsequently calculated in a known way in terms of its absorption values from the measured raw data with the aid of known methods that are stored in the illustrated program modules $P_1$ to $P_n$. According to the invention, it is possible to use all known 2D as well as 3D reconstruction methods in so doing, although it is common to all the methods that a weighting is undertaken using the data over the width B of the detector 5.

The remaining operation and control of the CT unit is likewise performed by way of the computer 7 and the keyboard 9. The calculated data can be output via the monitor 8 or a printer (not illustrated).

Figure 4:
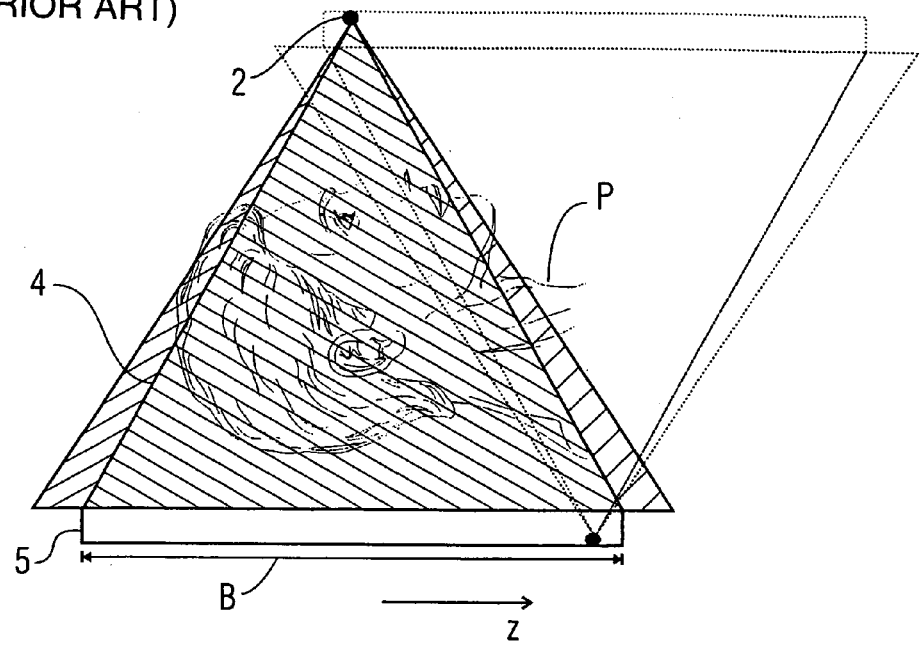
FIG. 4 shows conventional scanning with focus and detector opposite one another in the beam in conjunction with a gantry rotating in a spiral fashion, with feed in the z-direction.
Figure 5:
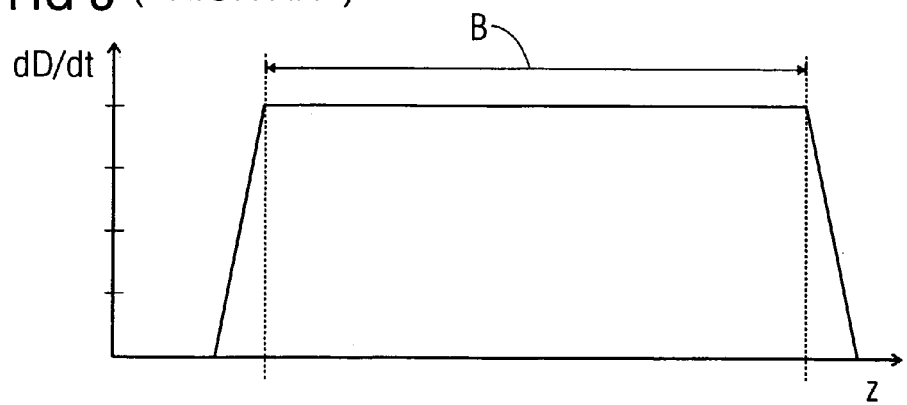
FIG. 5 shows the dose rate profile over the detector rows of the multirow detector from FIG. 4.
Figure 6:
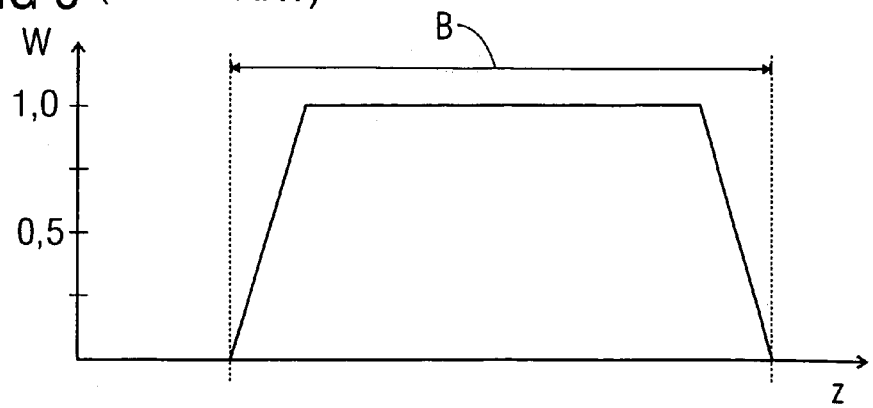
FIG. 6 shows a conventional characteristic of the weighting function W(q)

FIGS. 4 to 6 show the known situation of the geometric arrangement of the beam 4 relative to the detector 5, and the corresponding dose rate characteristic dD/dt over the width B of the detector with the position-dependent weighting W(z). FIG. 4 shows the schematic of the gantry 1 of the spiral CT with the focus 2 and the opposite detector 5, including the beam 4 emanating from the focus 2, respectively in the 0° position and—in a dotted representation—in a neighboring 180° position. In accordance with the nature of the spiral CT, these positions are additionally offset relative to one another by half the value of a feed for rotation in the z-direction.

At the edges—illustrated with a different hatching—the beam 4 has a penumbra which, however, does not touch the detector, so as to produce a plateau of the dose rate dD/dt that is as uniform as possible over the entire width B of the detector 5 in the z-direction.

The characteristic of the dose rate is shown in FIG. 5, the detector boundaries in the z-direction being indicated by dashes.

The characteristic of the weighing factor W(z) within the detector boundaries is shown in FIG. 6, situated thereunder, in a corresponding fashion relative to the z-axis. The weighting factor W(z) is approximated to the value 0 at the edges in order to avoid edge artifacts. This causes, on the one hand, ineffective use of the dose rate in the edge region of the detector and, on the other hand, an unnecessary radiation burden for the patient outside the detector.

It may be noted in addition that the spatial dependence of the weighting factor W(z) is denoted by W(q) when it is referred to the row number of the detector, without there being any change to the basic idea of an embodiment of the invention.

Figure 7:
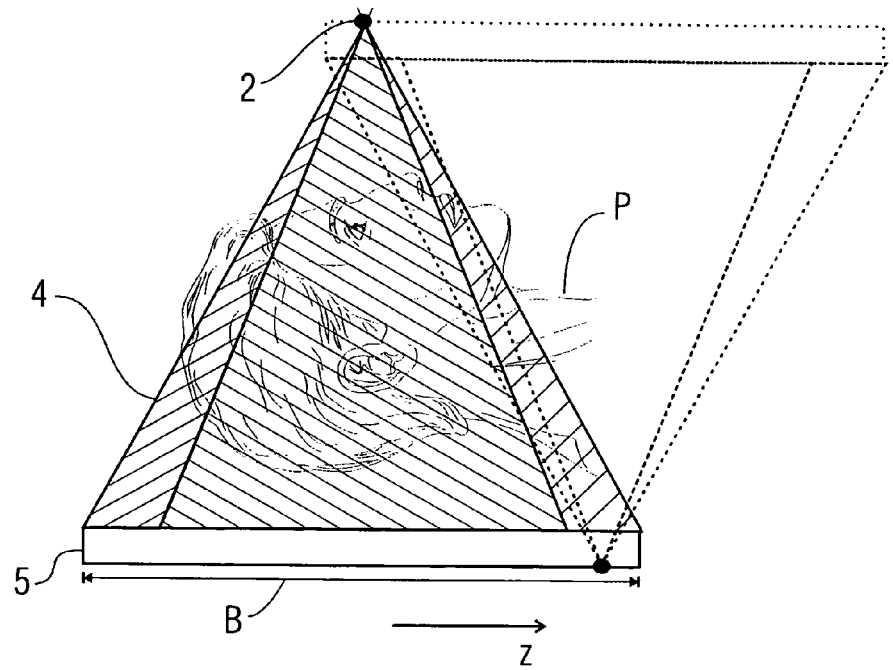
FIG. 7 shows spiral scanning with focus and detector opposite one another, the dose rate characteristic, decreasing at the edges, of the beam occurring on the detector.
Figure 8:
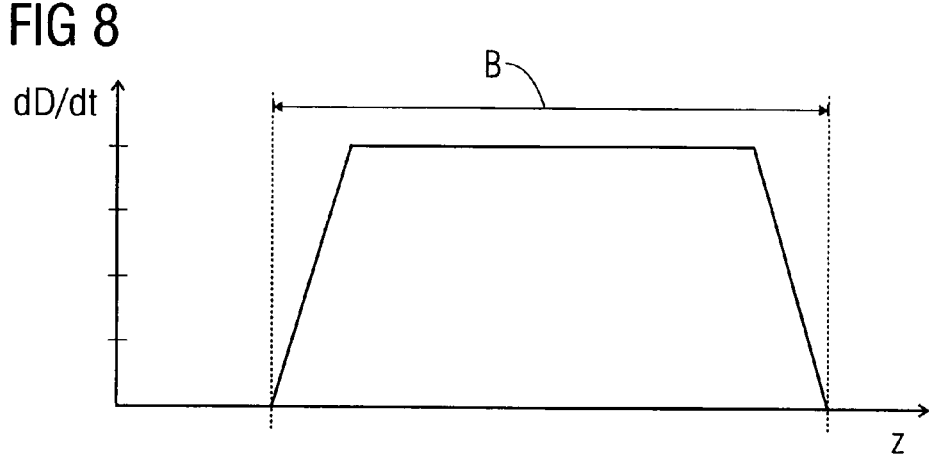
FIG. 8 shows a dose rate profile over the detector rows of the multirow detector from FIG. 7.
Figure 9:
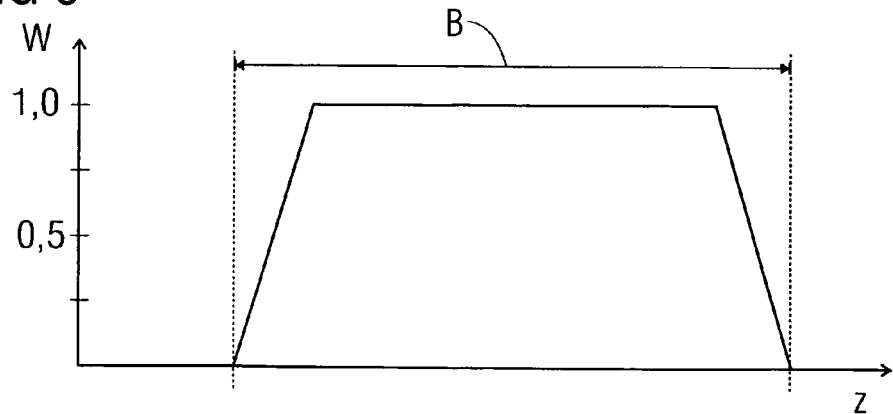
FIG. 9 shows the characteristic of the weighting function W(q) matched to the dose rate profile $\dot{D}(q)$.

According to an embodiment of the invention, as illustrated in FIGS. 7 to 9, the entire beam 4 is used and the weighting characteristic W(z) is matched to the dose rate characteristic dD/dt(z) over the detector. In a fashion corresponding to FIG. 4, FIG. 7 shows the schematic of a gantry of the spiral CT with the focus 2 and the opposite detector 5, including the beam 4 emanating from the focus 2, respectively in 0° position and—illustrated by dots—in a neighboring 180° position. Here, as well, the beam 4 has a differently hatched penumbra region at the edges, although the width B of the detector 5, and the extent of the overall beam 4 in the z-direction, including the penumbra regions on both sides, are tuned to one another such that ideally no radiation is output outside the detector 5.

Thus, counter to the preceding endeavors in the prior art, a drop in dose rate in the edge region of the detector is consciously not only accepted but even desired. Such an inventive characteristic of the dose rate is shown in FIG. 8 by way of example. The detector boundaries in the z-direction are again indicated by dashes. The characteristic of the weighting factor W(z) within the detector boundaries is shown in FIG. 9, situated thereunder, in a corresponding fashion relative to the z-axis.

According to an embodiment of the invention, the characteristic of the weighting factor W(z) is now matched to the spatial characteristic of the relative dose rate $dD/dt_{rel}(z)$— with $dD/dt_{rel}(z)=dD/dt/dD/dt_{max}$—so that, on the one hand, the weighting factor W(z) approaches the value 0 at the edges in order to avoid edge artifacts, while on the other hand also no dose rate is unnecessarily output to the patient. This results in better use of the dose rate in the edge region of the detector, and there is no unnecessary radiation burden on the patient outside the detector.

It is clear from comparing the width of the penumbra regions illustrated in FIGS. 4 and 7 that the penumbra region of the inventive design is more strongly marked than in the prior art. The reason for this is that the aim of the previous geometry was to keep the penumbra region as small as possible in order not to have to accept any unnecessary dose commitment of the patient. According to an embodiment of the invention, this is not required, or a larger penumbra region or at least a transitional region is even required, in order to be able thereby to match the characteristic of the weighting profile. This matching of the penumbra or of the edge profile of the dose rate distribution over the detector can be performed, on the one hand, by the additional use of shape filters, or else by bringing the diaphragm of the x-ray tube near the focus.

In addition to matching the characteristic of the dose rate and weighting factor, it is also possible for the characteristic of signal quality in the detector—caused by the existing dose rate and, if appropriate, additional other factors that can influence the signal quality—to be matched to the characteristic of the weighting factor.

The above-described exemplary embodiments relate to the medical application of the method according to the invention. However, the invention can also be applied outside medicine, for example in luggage inspection or material inspection.

It goes without saying that the abovementioned features of the invention can be used not only in the respectively specified combination, but also in other combinations or on their own, without departing from the scope of the invention.

In summary, thus, an embodiment of the invention proposes, on the one hand, a method for producing images with the aid of a spiral computed tomography unit and a weighted reconstruction in the case of which the detector and beam are tuned to one another in such a way that a drop in dose rate occurs at the edges within the detector and the form of the weighting function corresponds at least approximately to the dose rate characteristic and/or the characteristic of the signal quality of the detector. On the other hand, an improved spiral CT unit is also proposed in which the detector and beam are tuned to one another in such a way that a drop in dose rate occurs at the edges within the detector, and there are provided at least device(s) for weighting in the reconstruction whose characteristic in their value over the width of the detector corresponds to the characteristic of the dose rate and/or of the signal quality. An improvement in the dose usage for spiral CT is achieved by these measures.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for producing images in spiral computed tomography, comprising:

scanning an object to be examined, with at least one conical beam emanating from a focus, by moving the at least one focus around the object on a spiral focal track;

detecting, using at least one planar detector, the at least one beam, the at least one detector supplying output data corresponding to detected radiation; and reconstructing at least one of sectional and volume images of the scanned object from the output data, wherein at least one spatial weighting of the data used for calculation is undertaken for the purpose of reconstruction, wherein the at least one detector and at least one beam are tuned to one another in such a way that a drop in dose rate occurs at the edges within the detector, wherein a form of the weighting function corresponds at least approximately to at least one of the dose rate characteristic and to the characteristic of the signal quality of the detector and wherein the drop in dose rate occurs exclusively in the z-direction.

2. The method as claimed in claim 1, wherein the dose rate characteristic is achieved on the basis of the finite extent of the focus.

3. The method as claimed in claim 2, wherein the dose rate characteristic is designed in such a way that the dose rate vanishes at the edges.

4. The method as claimed in claim 2, wherein the weighting function assumes at least largely a trapezoidal characteristic.

5. The method as claimed in claim 1, wherein the dose rate characteristic is achieved by use of an appropriately designed shape filter between the focus and detector.

6. The method as claimed in claim 5, wherein the dose rate characteristic is designed in such a way that the dose rate vanishes at the edges.

7. The method as claimed in claim 5, wherein the weighting function assumes at least largely a trapezoidal characteristic.

8. The method as claimed in claim 1, wherein the dose rate characteristic is designed in such a way that the dose rate vanishes at the edges.

9. The method as claimed in claim 1, wherein the weighting function assumes at least largely a trapezoidal characteristic.

10. The method as claimed in claim 1, wherein the reconstruction method is a 2D reconstruction method.

11. The method as claimed in claim 1, wherein the reconstruction method is a 3D reconstruction method.

12. The method as claimed in claim 1, wherein the reconstruction method is a Segmented Multiple Plane Reconstruction.

13. A device for producing images in spiral computed tomography, comprising:

means for scanning an object to be examined, with at least one beam emanating from a focus;

means for detecting the at least one beam and for supplying output data corresponding to detected radiation; and means for reconstructing at least one of sectional and volume images of the scanned object from the output data, wherein at least one spatial weighting of the data used for calculation is undertaken for the purpose of reconstruction, wherein the means for detecting and the at least one beam are tuned to one another in such a way that a drop in dose rate occurs at the edges within the means for detecting, wherein a form of the weighting function corresponds at least approximately to at least one of the dose rate characteristic and to the characteristic of the signal quality of the means for detecting and wherein the drop in dose rate occurs exclusively in the z-direction.

14. The device as claimed in claim 13, wherein the dose rate characteristic is achieved on the basis of the finite extent of the focus.

15. The device as claimed in claim 13, wherein the dose rate characteristic is achieved by use of an appropriately designed shape filter between the focus and detector.

16. The device as claimed in claim 13, wherein the dose rate characteristic is designed in such a way that the dose rate vanishes at the edges.

17. The device as claimed in claim 13, wherein the weighting function assumes at least largely a trapezoidal characteristic.

18. The device as claimed in claim 13, wherein the reconstruction is a 2D reconstruction.

19. The device as claimed in claim 13, wherein the reconstruction is a 3D reconstruction.

20. The device as claimed in claim 13, wherein the reconstruction is a Segmented Multiple Plane Reconstruction.

* * * * *